United States Patent
Nomura et al.

(10) Patent No.: US 9,180,444 B2
(45) Date of Patent: Nov. 10, 2015

(54) METHOD FOR PRODUCING CATALYST FOR USE IN PRODUCTION OF METHYLAMINE COMPOUND, AND METHOD FOR PRODUCING METHYLAMINE COMPOUND

(71) Applicant: MITSUBISHI GAS CHEMICAL COMPANY, INC., Tokyo (JP)

(72) Inventors: Toshihiro Nomura, Niigata (JP); Katsumi Higuchi, Tokyo (JP); Akio Hashimoto, Okayama (JP); Sachiko Arie, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/433,500

(22) PCT Filed: Oct. 11, 2013

(86) PCT No.: PCT/JP2013/077706
§ 371 (c)(1),
(2) Date: Apr. 3, 2015

(87) PCT Pub. No.: WO2014/061569
PCT Pub. Date: Apr. 24, 2014

(65) Prior Publication Data
US 2015/0258538 A1    Sep. 17, 2015

(30) Foreign Application Priority Data
Oct. 15, 2012    (JP) .................................. 2012-228302

(51) Int. Cl.
| | | |
|---|---|---|
| *B01J 37/10* | (2006.01) | |
| *B01J 37/08* | (2006.01) | |
| *B01J 29/85* | (2006.01) | |
| *C07C 209/16* | (2006.01) | |
| *C07C 209/64* | (2006.01) | |

(52) U.S. Cl.
CPC *B01J 37/10* (2013.01); *B01J 29/85* (2013.01); *B01J 37/08* (2013.01); *C07C 209/16* (2013.01); *C07C 209/64* (2013.01)

(58) Field of Classification Search
None
See application file for complete search history.

(56) References Cited

U.S. PATENT DOCUMENTS

| | | | |
|---|---|---|---|
| 4,082,805 A | 4/1978 | Kaeding | |
| 4,205,012 A | 5/1980 | Parker et al. | |
| 4,254,061 A | 3/1981 | Weigert | |
| 4,313,003 A | 1/1982 | Weigert | |
| 4,436,938 A | 3/1984 | Tompsett | |
| 4,477,336 A | 10/1984 | Scherzer | |
| 4,578,516 A | 3/1986 | Ashina et al. | |
| 4,582,936 A | 4/1986 | Ashina et al. | |
| 4,683,334 A | 7/1987 | Bergna et al. | |
| 4,874,896 A | 10/1989 | Olson et al. | |
| 5,248,647 A | 9/1993 | Barger | |
| 6,153,798 A | 11/2000 | Hidaka et al. | |
| 6,180,828 B1 | 1/2001 | Hidaka et al. | |
| 7,015,174 B2 * | 3/2006 | Loezos et al. | 502/214 |
| 7,115,238 B2 * | 10/2006 | Higuchi et al. | 423/306 |
| 7,309,806 B2 * | 12/2007 | Loezos et al. | 585/639 |
| 2003/0171633 A1 | 9/2003 | Xu | |
| 2003/0176752 A1 | 9/2003 | Levin et al. | |
| 2003/0176753 A1 | 9/2003 | Levin et al. | |
| 2004/0030213 A1 | 2/2004 | Levin et al. | |
| 2005/0101818 A1 | 5/2005 | Levin et al. | |
| 2005/0202963 A1 | 9/2005 | Levin et al. | |
| 2005/0249661 A1 | 11/2005 | Higuchi et al. | |
| 2005/0255991 A1 | 11/2005 | Levin et al. | |
| 2006/0116517 A1 | 6/2006 | Bosch et al. | |
| 2007/0161840 A1 | 7/2007 | Xu | |

FOREIGN PATENT DOCUMENTS

| | | |
|---|---|---|
| JP | 54-148708 | 11/1979 |
| JP | 56-46846 | 4/1981 |
| JP | 56-113747 | 9/1981 |
| JP | 58-49340 | 3/1983 |
| JP | 58-69846 | 4/1983 |
| JP | 59-210050 | 11/1984 |
| JP | 59-227841 | 12/1984 |
| JP | 61-254256 | 11/1986 |
| JP | 2-734 | 1/1990 |
| JP | 11-35527 | 2/1999 |
| JP | 11-239729 | 9/1999 |
| JP | 2000-5604 | 1/2000 |
| JP | 2002-210374 | 7/2002 |

(Continued)

OTHER PUBLICATIONS

Search report from PCT/JP2013/077706, mail date is Jan. 14, 2014.
"Advanced Zeolites-Synthesis and Applications", pp. 83-92, Jul. 1999, cited and discussed in the specification at pp. 2, 3 with search result of the bibliographic information obtained from the National Diet Library.

*Primary Examiner* — Brian J Davis
(74) *Attorney, Agent, or Firm* — Greenblum & Bernstein, P.L.C.

(57) ABSTRACT

According to the present invention, a method for producing a catalyst for use in the production of a methylamine compound can be provided, wherein the catalyst comprises a modified crystalline silicoaluminophosphate salt molecular sieve. The method comprises: a moisture control step of adsorbing moisture onto a crystalline silicoaluminophosphate salt molecular sieve in an amount of 5 to 30 wt % of the crystalline silicoaluminophosphate salt molecular sieve; and a step of heating the crystalline silicoaluminophosphate salt molecular sieve having moisture adsorbed thereon under a pressure of 0.1 MPa or more and at a temperature of 130 to 350° C. for 5 to 40 hours.

8 Claims, No Drawings

(56) References Cited

FOREIGN PATENT DOCUMENTS

| JP | 2004-49987 | 2/2004 |
| JP | 2005-518930 | 6/2005 |
| JP | 2006-527150 | 11/2006 |
| JP | 4362363 | 8/2009 |
| JP | 4596116 | 10/2010 |
| WO | 03/000411 | 1/2003 |

* cited by examiner

METHOD FOR PRODUCING CATALYST FOR USE IN PRODUCTION OF METHYLAMINE COMPOUND, AND METHOD FOR PRODUCING METHYLAMINE COMPOUND

TECHNICAL FIELD

The present invention relates to a method for producing a catalyst for use in the production of a methylamine compound, the catalyst comprising a modified crystalline silicoaluminophosphate salt molecular sieve, and a method for producing a methylamine compound using a catalyst obtained by the method.

BACKGROUND ART

Methylamine compounds are usually produced from methanol and ammonia using a solid acid catalyst such as silica-alumina at a temperature of around 400° C. As is well known, use of the silica-alumina catalyst leads to predominant production of trimethylamine according to thermodynamic equilibrium although trimethylamine is least demanded among the three types of methylamines, namely, mono-, di- and tri-methylamines. However, dimethylamine accounts for most of the demand for methylamines, and least demanded trimethylamine is recycled for a reaction system after being subjected to separation from a reaction product by distillation, resulting in a very large amount of consumption energy. For this reason, recently, methods for selectively producing dimethylamine that overcome the thermodynamic equilibrium composition have been developed.

Examples of such methods include those using zeolites (crystalline aluminosilicate molecular sieves) such as Zeolite A (for example, see Patent Document 1), FU-1 (for example, see Patent Document 2), ZSM-5 (for example, see Patent Document 3), ferrierite and erionite (for example, see Patent Document 4), ZK-5, Rho, chabazite and erionite (for example, see Patent Document 5) and mordenite (for example, see Patent Documents 6, 7, 8 and 9). In these methods, zeolites having a small micropore channel size are further subjected to ion exchange, dealumination treatment, addition of a specific element, silylation treatment or the like in order to control the micropore channel size or modify acid sites on external surfaces thereof, thereby trying to improve dimethylamine selectivity and catalytic activity.

Further, for example, a method for producing a methylamine compound using a crystalline silicoaluminophosphate salt molecular sieve that overcomes the thermodynamic equilibrium composition (for example, see Patent Document 10) is also publicly known. The present inventors made researches on techniques of selectively producing dimethylamine and found that SAPOs modified with silica, SAPOs modified with various oxides and SAPOs in which an amorphous oxide layer having an appropriate thickness is formed on surfaces of crystal particles exhibit activity and dimethylamine selectivity higher than those of catalysts of prior art, and have already filed patent applications related thereto (for example, see Patent Documents 11, 12, 13 and 14). In addition, Patent Document 11 describes the production of dimethylamine by means of disproportionation of monomethylamine.

By such improvement of catalysts, the cost for the production of methylamines has been significantly improved compared to those of processes using conventional catalysts. However, from a practical viewpoint, long-term stability of catalytic performance is desired to be further improved, and temporal stability of dimethylamine selectivity and long-term maintenance of catalytic activity are desired.

Crystalline aluminosilicate molecular sieves and crystalline silicoaluminophosphate salt molecular sieves are sometimes modified by means of contact with water vapor for the purpose of the improvement of catalytic activity and selectivity when used as catalysts for the production of chemical products. For example, ultrastabilized Y-type zeolite (USY), which is used for fluid catalytic cracking (FCC), is obtained by being contacted with water vapor at 600 to 800° C. (for example, see Patent Document 15 and Non-patent Document 1). Further, Barger et al have reported that, when a crystalline silicoaluminophosphate salt molecular sieve is treated under water vapor atmosphere at 700 to 900° C., $C_2$-$C_3$ olefin selectivity and catalyst life are improved in a methanol conversion reaction (see Patent Document 16).

Modification of catalysts for methylamine synthesis by means of contact with water vapor is also publicly known. For example, Patent Document 9 describes that dimethylamine selectivity is improved by contacting a crystalline aluminosilicate molecular sieve such as mordenite with water vapor at 250 to 700° C. However, even though selectivity is improved, the effect thereof is not sufficient, and catalytic activity is sacrificed for the contact with water vapor.

Modification using water vapor is sometimes carried out for the purpose of the improvement of the strength of a molded body or removal of impurities in a catalyst. For example, Patent Document 17 discloses a method for improving the strength of a molded body comprising a crystalline aluminosilicate molecular sieve by means of the treatment under a flow of water vapor-containing gas at 100 to 600° C. Further, Patent Document 18 discloses a method in which a crystalline silicoaluminophosphate salt molecular sieve molded using a halogen-containing binder is contacted with water vapor at 400 to 1000° C. to remove halogen in the catalyst. The documents disclose that these catalysts can be used for methylamine synthesis reaction, but do not describe any effect on catalytic activity and selectivity.

As described above, there are many reports regarding methods for modifying crystalline aluminosilicate molecular sieves and crystalline silicoaluminophosphate salt molecular sieves by means of the contact with water vapor, but no convenient and effective method has been found for improving catalytic activity and selectivity in the production of methylamines and maintaining activity and selectivity for a long period of time.

PRIOR ART DOCUMENTS

Patent Documents

Patent Document 1: Japanese Laid-Open Patent Publication No. S58-69846
Patent Document 2: Japanese Laid-Open Patent Publication No. S54-148708
Patent Document 3: U.S. Pat. No. 4,082,805
Patent Document 4: Japanese Laid-Open Patent Publication No. S56-113747
Patent Document 5: Japanese Laid-Open Patent Publication No. S61-254256
Patent Document 6: Japanese Laid-Open Patent Publication No. S56-46846
Patent Document 7: Japanese Laid-Open Patent Publication No. S58-49340
Patent Document 8: Japanese Laid-Open Patent Publication No. S59-210050

Patent Document 9: Japanese Laid-Open Patent Publication No. S59-227841
Patent Document 10: Japanese Laid-Open Patent Publication No. H02-734
Patent Document 11: Japanese Laid-Open Patent Publication No. H11-35527
Patent Document 12: Japanese Laid-Open Patent Publication No. H11-239729
Patent Document 13: Japanese Laid-Open Patent Publication No. 2000-5604
Patent Document 14: Japanese Patent No. 4596116
Patent Document 15: U.S. Pat. No. 4,477,336
Patent Document 16: U.S. Pat. No. 5,248,647
Patent Document 17: Japanese National-phase PCT Publication No. 2006-527150
Patent Document 18: Japanese Patent No. 4362363

NON-PATENT DOCUMENTS

Non-Patent Document 1: Synthesis and application of functional zeolite (Japanese), pp. 83-92

SUMMARY OF THE INVENTION

Problems to be Solved by the Invention

The problem to be solved by the present invention is to provide a method for producing a catalyst for use in the production of a methylamine compound comprising a crystalline silicoaluminophosphate salt molecular sieve, which enables maintenance of high dimethylamine selectivity and long-term continuous use of a catalyst, and a more efficient method for producing a methylamine compound using the catalyst obtained by the production method.

Means for Solving the Problems

The present inventors diligently made researches in order to solve the above-described problem, and found that a catalyst for use in the production of a methylamine compound comprising a modified crystalline silicoaluminophosphate salt molecular sieve, which maintains high dimethylamine selectivity and low trimethylamine selectivity and further realizes little reduction in the activity due to long-term use, can be obtained by adsorbing moisture onto a crystalline silicoaluminophosphate salt molecular sieve in an amount of 5 to 30 wt % of the crystalline silicoaluminophosphate salt molecular sieve and subsequently heating it under a pressure of 0.1 MPa or more and at a temperature of 130 to 350° C. for 5 to 40 hours for modification, and thus the present invention was achieved.

Specifically, the present invention includes the below-described embodiments.

<1> A method for producing a catalyst for use in the production of a methylamine compound, the catalyst comprising a modified crystalline silicoaluminophosphate salt molecular sieve, wherein the method comprises:
a moisture control step of adsorbing moisture onto a crystalline silicoaluminophosphate salt molecular sieve in an amount of 5 to 30 wt % of the crystalline silicoaluminophosphate salt molecular sieve; and
a step of heating the crystalline silicoaluminophosphate salt molecular sieve having moisture adsorbed thereon under a pressure of 0.1 MPa or more and at a temperature of 130 to 350° C. for 5 to 40 hours (hereinafter sometimes referred to as a "thermal modification step").

<2> The method for producing a catalyst for use in the production of a methylamine compound according to item <1>, wherein the crystalline silicoaluminophosphate salt molecular sieve is at least one selected from SAPO-14, 17, 18, 21, 22, 25, 33, 34, 35, 39, 42, 43, 44, 47, 52 and 56.

<3> The method for producing a catalyst for use in the production of a methylamine compound according to item <1> or <2>, wherein the crystalline silicoaluminophosphate salt molecular sieve comprises at least one type of element selected from among Mg, Ca, Sr, Y, Ti, Zr, V, Nb, Cr, Mn, Fe, Ru, Co, Rh, Ir, Ni, Pd, Pt, Cu, Zn, B, Ga, In, Ge and Sn.

<4> The method for producing a catalyst for use in the production of a methylamine compound according to any one of items <1> to <3>, wherein the moisture control step of adsorbing moisture onto the crystalline silicoaluminophosphate salt molecular sieve includes filling a reactor with the crystalline silicoaluminophosphate salt molecular sieve and continuously flowing a moisture-containing gas through a packed bed of the crystalline silicoaluminophosphate salt molecular sieve to be brought into contact therewith, and wherein the crystalline silicoaluminophosphate salt molecular sieve is brought into contact with the moisture-containing gas at a temperature higher than a dew point thereof.

<5> The method for producing a catalyst for use in the production of a methylamine compound according to item <4>, wherein the moisture-containing gas is a mixed gas of water vapor and at least one selected from an inert gas and air.

<6> A method for producing a methylamine compound which comprises performing a reaction between methanol and ammonia in the presence of a catalyst for use in the production of a methylamine compound comprising a crystalline silicoaluminophosphate salt molecular sieve, wherein the catalyst is produced by the method for producing a catalyst for use in the production of a methylamine compound according to any one of items <1> to <5>.

<7> A method for producing a methylamine compound which comprises performing a reaction between methanol and monomethylamine or a reaction between methanol, ammonia and monomethylamine in the presence of a catalyst for use in the production of a methylamine compound comprising a crystalline silicoaluminophosphate salt molecular sieve, wherein the catalyst is produced by the method for producing a catalyst for use in the production of a methylamine compound according to any one of items <1> to <5>.

<8> A method for producing a methylamine compound which comprises performing a disproportionation reaction of monomethylamine in the presence of a catalyst for use in the production of a methylamine compound comprising a crystalline silicoaluminophosphate salt molecular sieve, wherein the catalyst is produced by the method for producing a catalyst for use in the production of a methylamine compound according to any one of items <1> to <5>.

Advantageous Effect of the Invention

According to the present invention, it is possible to homogeneously modify a crystalline silicoaluminophosphate salt molecular sieve catalyst, which was difficult to realize by the conventional modification method using water vapor, and therefore, in a methylamine synthesis reaction, the activity and the selectivity can be improved, and the activity and the selectivity can be maintained for a long period of time. Moreover, by carrying out modification by 2 steps, specifically, a moisture control step and a thermal modification step, such modification can be carried out under conditions milder than those for the conventional modification method.

EMBODIMENTS FOR CARRYING OUT THE INVENTION

Hereinafter, the present invention will be described in detail.

A crystalline silicoaluminophosphate salt molecular sieve is a compound having a three-dimensional microporous crystal framework structure of $PO_2^+$, $AlO_2^-$ and $SiO_2$ tetrahedral units, which is crystalline and microporous, as described in U.S. Pat. No. 4,440,871, and it is called "SAPO". Further, compounds having a three-dimensional microporous crystal framework structure including tetrahedral units of a metal other than silicon, aluminum and phosphorus are disclosed in EP Patent No. 159,624, etc., and such a compound is called "ELAPSO molecular sieve". SAPO and ELAPSO with various structures, in which the micropore diameter and the connection pattern of micropores vary depending on the arrangement of the aforementioned tetrahedral units, are known. SAPO to be used for producing the catalyst for use in the production of a methylamine compound of the present invention includes ELAPSO.

In order to selectively obtain a methylamine compound, in particular, monomethylamine and dimethylamine in a reaction between methanol and ammonia, the effective micropore diameter of SAPO is desirably in the range of 0.3 to 0.6 nm. Since such a micropore inhibits the passage of trimethylamine molecules and permits the passage of monomethylamine and dimethylamine which have a smaller molecular size, the selectivity of the reaction is eventually predominated by monomethylamine and dimethylamine (D. R. Corbin, S. Schwarz, and G. C. Sonnichsen, Catalysis Today, 37 (1997), pp. 71-102). The aforementioned effective micropore diameter corresponds to diameters of 8 to 10-oxygen-membered ring micropores of SAPO, but in particular, SAPO having 8-oxygen-membered ring micropores is preferred because it is suitable for reducing the trimethylamine selectivity to a lower level.

Examples of SAPOs having 8-oxygen-membered ring micropores include SAPO-14, 17, 18, 21, 22, 25, 33, 34, 35, 39, 42, 43, 44, 47, 52 and 56. The relationship between the number attached to each of these SAPOs and the IUPAC structural code specified by the Structure Commission of the International Zeolite Association (IZA) is described, for example, in "Atlas of Zeolite Framework Types" edited by the Structure Commission of the International Zeolite Association, published by Elsevier. The aforementioned SAPOs respectively correspond to AFN, ERI, AEI, AWO, AWW, ATV, ATT, CHA, LEV, ATN, LTA, GIS, CHA, CHA, AFT and AFX of the IUPAC structural code. Among the aforementioned SAPOs, SAPO-17, 18, 34, 35, 44, 47 and 56 are more preferred, and SAPO-34, which has the CHA-type structure, is particularly preferred.

The SAPO to be used in the present invention may contain at least one type of element selected from among Mg, Ca, Sr, Y, Ti, Zr, V, Nb, Cr, Mn, Fe, Ru, Co, Rh, Ir, Ni, Pd, Pt, Cu, Zn, B, Ga, In, Ge and Sn. The case where SAPOs contain an element selected from among Mg, Y, Ti, Zr, Mn, Fe, Co and Sn is more preferred, and Ti and Zr are particularly preferred because these elements have the effect of improving catalytic activity and life performance. These elemental components may be present in and/or outside the three-dimensional microporous crystal framework structure.

The above-described SAPOs are synthesized by the hydrothermal synthesis method generally known in this technical field. For example, SAPO-34 having the CHA-type structure can be synthesized by using tetraethyl ammonium hydroxide as a template and hydrothermally treating a mixture of a silicon compound, an aluminum compound, a phosphorous compound and water. Further, SAPOs containing an element other than silicon, aluminum and phosphorous can be synthesized by hydrothermally treating a mixture of a template, a silicon compound, an aluminum compound, a phosphorous compound, water, and nitrate, sulfate, chloride, oxide sol, oxide powder, alkoxide and/or complex of the metal element other than silicon, aluminum and phosphorous.

The SAPO to be used in the present invention may have an amorphous oxide layer composed of oxides comprising silicon, aluminum and phosphorus. Further, the SAPO may be one modified with an oxide or one silica-modified with an organic silicon compound.

The form of the SAPO to be used in the present invention is not particularly limited and may be the powder form or granule form, and also may be a molded body obtained by an extrusion molding method, tablet compression method or the like.

The SAPO to be used in the production of the catalyst for use in the production of a methylamine compound is a SAPO modified by a moisture control step of adsorbing an appropriate amount of moisture onto the SAPO homogeneously and a thermal modification step of thermally treating it under an appropriate pressure and at an appropriate temperature for a predetermined amount of time.

Firstly, the moisture control step will be described in detail. The amount of moisture to be adsorbed onto SAPO (amount of moisture control) in the present invention is preferably 5 to 30 wt %, and particularly preferably 10 to 25 wt % of the dry weight of SAPO. This is because, when the amount of moisture control is less than 5 wt %, the trimethylamine selectivity in a methylamine synthesis reaction using methanol and ammonia is high, and therefore the monomethylamine selectivity and dimethylamine selectivity become low. Meanwhile, when the amount of moisture control is more than 30 wt %, the methanol conversion rate in the aforementioned methylamine synthesis reaction becomes low. In this regard, the dry weight of SAPO is a weight when drying SAPO in a drier at 110° C. until weight change stops.

The method for adsorbing moisture onto SAPO (moisture control method) is not particularly limited, but it is preferred to perform contact between SAPO and a moisture-containing gas. Examples of the moisture control method include a method in which SAPO and a predetermined amount of water are arranged in an airtight container such as a steam furnace and an autoclave so as not to directly contact with each other, allowed to stand until all water is adsorbed onto SAPO. In this case, in order to promote adsorption of moisture onto SAPO, the airtight container containing SAPO and the predetermined amount of water may be heated at a temperature of 50 to 120° C. Note that a method of mixing and contacting SAPO with liquid water is preferably employed as little as possible because a molded body may be broken and a reactive point may be deteriorated by rapid generation of adsorption heat and the amount of moisture in SAPO tends to become inhomogeneous.

A practical and particularly preferred moisture control method is a method in which a reactor for performing the methylamine synthesis reaction is filled with SAPO and a moisture-containing gas is continuously flowed through a packed bed of SAPO to be brought into contact therewith. In this regard, by performing the contact between SAPO and the moisture-containing gas at a temperature higher than a dew point thereof, moisture can be adsorbed up to the saturated adsorption amount of moisture on SAPO, which is determined by the temperature and water vapor partial pressure.

Specifically, the reactor is filled with SAPO, and a mixed gas of water vapor and an inert gas and/or air having a moisture concentration of 3 to 100 vol %, more preferably 10 to 80 vol % is continuously flowed through the packed bed of SAPO under a pressure of atmospheric pressure to 0.5 MPa, more preferably under atmospheric pressure, and at 80 to 130° C., more preferably 100 to 120° C. The type of the reactor is not particularly limited, and any of heat insulation-type, tubular-type and multitubular-type reactors may be used. Further, the type of the inert gas is not particularly limited, and for example, nitrogen, helium, argon or the like can be used.

The isothermal adsorption property of SAPO is utilized in the moisture control method of continuously flowing the moisture-containing gas through the packed bed of SAPO. Therefore, the temperature of the inside of the packed bed of SAPO during the moisture control treatment is desirably controlled homogeneously, and the difference of the temperature of the inside of the packed bed of SAPO at the end of moisture control is preferably set to 5° C. or less, and particularly preferably set to 2° C. or less. In this case, there is almost no difference between the moisture concentration at the inlet of the reactor and the moisture concentration at the outlet of the reactor. Further, in order to set the amount of moisture adsorbed onto SAPO to be homogeneous, the differential pressure between the inlet and the outlet of the reactor at the time of flowing the moisture-containing gas is preferably controlled to 50 KPa or less.

When supplying the moisture-containing gas to the packed bed of SAPO, heat generation of the packed bed of SAPO caused by moisture adsorption may be increased depending on the moisture content of SAPO and the moisture concentration of the gas to be contacted with the packed bed of SAPO. Since a molded body may be broken and a reactive point may be deteriorated due to rapid heat generation of the packed bed of SAPO, temperature elevation due to adsorption heat is preferably suppressed to less than 20° C. from the temperature for performing moisture control, and it is preferred that the moisture concentration of the gas is set to be lower than that in the aforementioned range at the beginning of supply, then generally increased depending on the amount of heat generation of the packed bed of SAPO, and controlled to be in the aforementioned range finally.

Next, the thermal modification step will be described in detail. In the present invention, SAPO subjected to moisture control so that the moisture content becomes homogeneous in the moisture control step described above is subjected to the heat treatment at an appropriate temperature under an appropriate pressure for a predetermined amount of time, thereby modifying SAPO. The heat treatment temperature is preferably 130 to 350° C., and more preferably 150 to 200° C. This is because modification is slow at a heat treatment temperature of lower than 130° C., resulting in high trimethylamine selectivity in the methylamine synthesis reaction using methanol and ammonia. Meanwhile, when the heat treatment temperature is higher than 350° C., SAPO is excessively modified, and therefore, the methanol conversion rate in the methylamine synthesis reaction becomes low, or the trimethylamine selectivity becomes high.

The pressure during the heat treatment is sufficient when moisture adsorbed onto SAPO by the moisture control treatment can be evaporated to a limited extent, and therefore, it is sufficient when the pressure is 0.1 MPa or more. The upper limit of the pressure is not particularly limited, but it is economical when the pressure is less than 5 MPa from an industrial viewpoint, and more preferably, the pressure is 0.1 to 2 MPa. The method for controlling the pressure during the heat treatment is not particularly limited. For example, increase in the internal pressure of an apparatus caused by heating for increasing the heat treatment temperature may be utilized, or the pressure may be increased and controlled using an inert gas such as nitrogen, helium and argon or air. In this case, a pressure control valve may be further used to control the pressure to an appropriate level.

The heat treatment time is preferably 5 to 40 hours, and more preferably 10 to 30 hours. This is because, when the treatment time is less than 5 hours, modification is insufficient, resulting in high trimethylamine selectivity in the methylamine synthesis reaction using methanol and ammonia. Meanwhile, when the treatment time is more than 40 hours, SAPO is excessively modified, and therefore, the methanol conversion rate in the methylamine synthesis reaction becomes low.

The apparatus to be used for thermal modification is sufficient when it can control the temperature and pressure to the levels at the time of the heat treatment. For example, an airtight container such as a steam furnace and an autoclave, a reactor equipped with a pressure control valve or the like can be used. In this regard, thermal modification is carried out in a manner such that the ratio between the volume of the packed bed of SAPO and the volume of the space in the apparatus preferably becomes 10 or less, and more preferably becomes 5 or less.

At the time of thermal modification, the airtight container such as a steam furnace and an autoclave and the reactor for the methylamine synthesis reaction used in the above-described moisture control treatment may be continuously used. Alternatively, SAPO subjected to the moisture control treatment may be transferred into another apparatus. In the case where thermal modification is carried out after SAPO subjected to the moisture control treatment is transferred into another apparatus, SAPO can be modified without difficulty if it is handled in a manner such that the moisture content of SAPO does not change.

As described above, it is possible to homogeneously modify SAPO, which was difficult to realize by the conventional modification method using water vapor, by homogeneously adsorbing an appropriate amount of moisture onto SAPO and then modifying it by means of the heat treatment at an appropriate temperature under an appropriate pressure for a predetermined amount of time, and therefore, in the methylamine synthesis reaction, the activity and the selectivity can be improved, and the activity and the selectivity can be maintained for a long period of time. Moreover, by carrying out modification by the 2 steps, specifically, the moisture control step and the thermal modification step, such modification can be carried out under conditions milder than those for the conventional modification method.

The thermally modified SAPO can be directly used in the methylamine synthesis reaction, but it is more preferred that SAPO is used in the reaction after removing a part or all of the moisture adsorbed onto SAPO by means of the drying treatment. In the case where SAPO is thermally modified using a reactor for methylamine synthesis, the moisture adsorbed onto SAPO can be removed by releasing the pressure after thermal modification and flowing a dry gas such as an inert gas and air through the packed bed of SAPO.

SAPO modified by the method of the present invention can be used as a catalyst for the production of a methylamine compound in which a reaction such as a reaction between methanol and ammonia, a reaction between methanol and monomethylamine and a disproportionation reaction of monomethylamine is performed. The type of the reaction may be the fixed bed type or fluid bed type. The reaction temperature is preferably 200 to 400° C., and particularly preferably 250 to 350° C. The reaction pressure is not particularly limited, but usually, the reaction is preferably performed under a pressure of 0.1 to 5 MPa.

EXAMPLES

Hereinafter, the present invention will be specifically described by way of examples and comparative examples. However, the present invention is not limited only to these examples.

Regarding SAPO and metal-containing SAPO used in the examples and comparative examples, those synthesized according to Example 1 (synthesis of SAPO-34) and Example 6 (synthesis of Ti-containing SAPO-34) described in Patent Document 14 were granulated to have a grain size of 1 to 2 mm and then used. Further, the moisture control method (static, continuous), the heat treatment method, the methylamine synthesis reaction and the method for analyzing a reaction product are as described below.

(1) Moisture Control Method (Static):

A predetermined amount of SAPO dried in a drier at 110° C. in advance until weight change stopped and water corresponding to the target amount of moisture control were respectively weighed and put on different magnetic plates, and the plates were placed in a desiccator and it was sealed. The desiccator was heated in a drier at 110° C., and 2 hours later, it was taken out from the drier and cooled to room temperature. The method for calculating the amount of moisture control is as follows:

Amount of moisture control of SAPO (wt %)=(Weight of SAPO after moisture control−Weight of dried SAPO before moisture control)/Weight of dried SAPO before moisture control×100

(2) Moisture Control Method (Continuous):

A reaction tube having an inner diameter of 13 mmϕ and a length of 30 cm was weighed in advance, a pressure gauge, a nitrogen supply valve and a steam supply valve were attached to the upper portion of the reaction tube, a gas shutoff valve was attached to the lower portion of the reaction tube, and then moisture control was carried out. 10 g of dried SAPO was put into the reaction tube, and the reaction tube was heated with an aluminum block heater. A predetermined amount of water vapor and nitrogen were supplied from the upper portion of the reaction tube, and the conditions of temperature, pressure and moisture content were maintained until adsorption and desorption of moisture became equilibrated and the temperature distribution of the SAPO layer became constant. The amount of moisture control was obtained by weighing the reaction tube after the completion of moisture control and making calculation based on the amount of moisture adsorbed onto SAPO.

(3) Heat Treatment Method:

A SUS tube having an inner diameter of 10 mm and a length of 30 cm was used. The tube portion was heated with a mantle heater, a pressure gauge, a valve for nitrogen pressurization and a pressure control valve were attached to the upper portion of the tube, and the lower portion of the tube was shut by a plug. About 4 g (about 7 ml) of SAPO was put into the tube, and then the entire SUS tube was heated with the mantle heater. After a predetermined amount of time, the pressure in the SUS tube was dropped and SAPO was taken out from the tube. Note that SAPO was dried again at 110° C. before use in the methylamine synthesis reaction.

(4) Methylamine Synthesis Reaction:

A reaction tube having an inner diameter of 13 mmϕ and a length of 30 cm was filled with 2.5 g (3.5 ml) of dried SAPO after moisture control and heat treatment, the pressure was increased to 2 MPa, and then the temperature was elevated to 305° C. After that, a mixed raw material of methanol and ammonia having a weight ratio of 1 was supplied at 8.62 g/hour and at a space velocity (GHSV) of 2500 $h^{-1}$, thereby performing the methylamine synthesis reaction.

(5) Method for Analyzing a Reaction Product:

A reaction solution was collected as an aqueous solution, and after that, it was analyzed with GC-FID manufactured by Shimadzu Corporation, using a capillary column CP-Volamine.

The amount of moisture control of the catalyst and the conditions for the heat treatment of each of Examples 1-9 and Comparative Examples 1-5 are shown in Table 1, the results of the methylamine synthesis reaction are shown in Tables 2, 3 and 5, and the results of the disproportionation reaction of monomethylamine are shown in Table 4.

Example 1

4.00 g of dried SAPO-34 was subjected to the moisture control with 0.62 g of water according to the above-described moisture control method (static). The weight of SAPO taken out after cooling was 4.62 g, and the amount of moisture control was 15.5 wt %. Subsequently, a SUS tube for the heat treatment was filled with the obtained SAPO, and it was subjected to the heat treatment at 170° C. for 20 hours. At that time, the internal pressure was 0.3 MPa. After the heat treatment was completed, the pressure was dropped, and SAPO was dried at 110° C. for 2 hours and then used in the methylamine synthesis reaction. The reaction results obtained 24 hours after the initiation of the reaction were as follows: methanol conversion rate: 92 wt %, monomethylamine selectivity: 35 wt %, dimethylamine selectivity: 60 wt %, and trimethylamine selectivity: 5 wt %. Further, the reaction results obtained 240 hours later were as follows: methanol conversion rate: 90 wt %, monomethylamine selectivity: 38 wt %, dimethylamine selectivity: 59 wt %, and trimethylamine selectivity: 3 wt %.

Example 2

A SUS tube was filled with SAPO-34 subjected to the moisture control (10.2 wt %) according to the above-described moisture control method (static), the pressure was increased to 1 MPa with nitrogen, and then it was subjected to the heat treatment at 250° C. for 15 hours. After the heat treatment, the catalyst was taken out and dried at 110° C., and then used in the methylamine synthesis reaction. The reaction results are shown in Table 2.

Example 3

A SUS tube was filled with SAPO-34 subjected to the moisture control (25.4 wt %) according to the above-described moisture control method (static), the pressure was increased to 2 MPa with nitrogen, and then it was subjected to the heat treatment at 140° C. for 20 hours. After the heat treatment, the catalyst was taken out and dried at 110° C., and then used in the methylamine synthesis reaction. The reaction results are shown in Table 2.

Example 4

A SUS tube was filled with SAPO-34 subjected to the moisture control (15.3%) according to the above-described moisture control method (static), the pressure was increased to 2 MPa with nitrogen, and then it was subjected to the heat treatment at 320° C. for 15 hours. After the heat treatment, the catalyst was taken out and dried at 110° C., and then used in the methylamine synthesis reaction. The reaction results are shown in Table 2.

Example 5

A SUS tube was filled with SAPO-34 subjected to the moisture control (16.0 wt %) according to the above-described moisture control method (static), the pressure was increased to 1.5 MPa with nitrogen, and then it was subjected to the heat treatment at 170° C. for 20 hours. After the heat treatment, the catalyst was taken out and dried at 110° C., and then used in the methylamine synthesis reaction. The reaction results are shown in Table 2.

Example 6

A SUS tube was filled with SAPO-34 subjected to the moisture control (15.4%) according to the above-described moisture control method (static), and it was subjected to the heat treatment at 170° C. for 10 hours. At that time, the internal pressure was 0.3 MPa. After the heat treatment, the catalyst was taken out and dried at 110° C., and then used in the methylamine synthesis reaction. The reaction results are shown in Table 2.

Example 7

A SUS tube was filled with SAPO-34 subjected to the moisture control (15.3%) according to the above-described moisture control method (static), and it was subjected to the heat treatment at 170° C. for 35 hours. At that time, the internal pressure was 0.3 MPa. After the heat treatment, the catalyst was taken out and dried at 110° C., and then used in the methylamine synthesis reaction. The reaction results are shown in Table 2.

Example 8

The moisture control was carried out according to the above-described moisture control method (continuous). 10 g of dried SAPO-34 was put into a reaction tube, the temperature of the SAPO layer was set to 112° C., and a mixed gas was supplied at a nitrogen flow rate of 60 ml/min and a water vapor flow rate of 2.02 g/h until the temperature of the SAPO layer became constant. The amount of moisture control of SAPO calculated based on increase in the weight was 15.4 wt %. After the moisture control was completed, a steam supply valve and a nitrogen supply valve at the upper portion of the reaction tube and a gas shutoff valve at the lower portion of the reaction tube were closed, and in that state, SAPO was heated to 170° C. and subjected to the heat treatment for 15 hours. The internal pressure during the heat treatment was 0.3 MPa. After the heat treatment, SAPO was dried at 110° C. and then used in the methylamine synthesis reaction. The reaction results are shown in Table 2.

Example 9

The moisture control and the heat treatment were carried out in a manner similar to that in Example 1, except that Ti-containing SAPO-34 was used instead of SAPO-34, and the obtained SAPO was used in the methylamine synthesis reaction. The reaction results are shown in Table 2.

Comparative Example 1

Dried SAPO-34 was used in the methylamine synthesis reaction without being subjected to the moisture control and the heat treatment. The reaction results are shown in Table 2.

Comparative Example 2

A SUS tube was filled with SAPO-34 subjected to the moisture control (16.2 wt %) according to the above-described moisture control method (static), and it was subjected to the heat treatment at 170° C. for 1 hour. At that time, the internal pressure was 0.3 MPa. After the heat treatment, the catalyst was taken out and dried at 110° C., and then used in the methylamine synthesis reaction. The reaction results are shown in Table 2.

Comparative Example 3

A SUS tube was filled with SAPO-34 subjected to the moisture control (16.9 wt %) according to the above-described moisture control method (static), and it was subjected to the heat treatment at 170° C. for 60 hours. At that time, the internal pressure was 0.3 MPa. After the heat treatment, the catalyst was taken out and dried at 110° C., and then used in the methylamine synthesis reaction. The reaction results are shown in Table 2.

Comparative Example 4

A SUS tube was filled with SAPO-34 subjected to the moisture control (3.1 wt %) according to the above-described moisture control method (static), the pressure was increased to 2 MPa with nitrogen, and then it was subjected to the heat treatment at 100° C. for 20 hours. After the heat treatment, the catalyst was taken out and dried at 110° C., and then used in the methylamine synthesis reaction. The reaction results are shown in Table 2.

Comparative Example 5

A SUS tube was filled with SAPO-34 subjected to the moisture control (25.5 wt %) according to the above-described moisture control method (static), the pressure was increased to 7 MPa with nitrogen, and then it was subjected to the heat treatment at 400° C. for 15 hours. After the heat treatment, the catalyst was taken out and dried at 110° C., and then used in the methylamine reaction. The reaction results are shown in Table 2.

Example 10

Using SAPO-34 subjected to the moisture control and the heat treatment in a manner similar to that in Example 1, the methylamine synthesis reaction using methanol, monomethylamine and ammonia was performed. The reaction temperature was 300° C., and methanol, monomethylamine and ammonia were supplied respectively at 1.60 g/h, 1.37 g/h and 2.39 g/h and at a space velocity (GHSV) of 1500 The reaction results obtained 24 hours later and 240 hours later are shown in Table 3.

Comparative Example 6

The methylamine synthesis reaction was performed using SAPO-34 of Comparative Example 1 under the same conditions as those in Example 10. The reaction results are shown in Table 3.

Example 11

The disproportionation reaction of monomethylamine was performed using SAPO-34 subjected to the moisture control and the heat treatment in a manner similar to that in Example 1. The reaction temperature was 300° C., and the supply of monomethylamine was 3000 h$^{-1}$ (GHSV). The reaction results obtained 6 hours later and 240 hours later are shown in Table 4.

Comparative Example 7

The disproportionation reaction of monomethylamine was performed using SAPO-34 of Comparative Example 1 under the same conditions as those in Example 11. The reaction results are shown in Table 4.

Example 12

Using SAPO-34 subjected to the moisture control and the heat treatment in a manner similar to that in Example 1, the methylamine synthesis reaction using methanol and monomethylamine was performed. The reaction temperature was 320° C., and methanol and monomethylamine were supplied respectively at 1.17 g/h and 4.69 g/h and at a space velocity (GHSV) of 1200 h$^{-1}$. The reaction results obtained 24 hours later and 240 hours later are shown in Table 5.

Comparative Example 8

The methylamine synthesis reaction was performed using SAPO-34 of Comparative Example 1 under the same conditions as those in Example 12. The reaction results are shown in Table 5.

TABLE 1

| Section | SAPO | Amount of moisture control (wt %) | Heat treatment temperature (° C.) | Heat treatment time (h) | Internal pressure for heat treatment (MPa) |
|---|---|---|---|---|---|
| Example 1 | SAPO-34 | 15.5 | 170 | 20 | 0.3 |
| Example 2 | SAPO-34 | 10.2 | 250 | 15 | 1 |
| Example 3 | SAPO-34 | 25.4 | 140 | 20 | 2 |
| Example 4 | SAPO-34 | 15.3 | 320 | 15 | 2 |
| Example 5 | SAPO-34 | 16.0 | 170 | 20 | 1.5 |
| Example 6 | SAPO-34 | 15.4 | 170 | 10 | 0.3 |
| Example 7 | SAPO-34 | 15.3 | 170 | 35 | 0.3 |
| Example 8 | SAPO-34 | 15.4 | 170 | 15 | 0.3 |
| Example 9 | Ti-containing SAPO-34 | 15.5 | 170 | 20 | 0.3 |
| Comparative Example 1 | SAPO-34 | — | — | — | — |
| Comparative Example 2 | SAPO-34 | 16.2 | 170 | 1 | 0.3 |
| Comparative Example 3 | SAPO-34 | 16.9 | 170 | 60 | 0.3 |
| Comparative Example 4 | SAPO-34 | 3.1 | 100 | 20 | 2 |
| Comparative Example 5 | SAPO-34 | 25.5 | 400 | 15 | 7 |

TABLE 2

| | 24 hours later | | | | 240 hours later | | | |
|---|---|---|---|---|---|---|---|---|
| Section | Methanol conversion rate (wt %) | Monomethyl-amine selectivity (wt %) | Dimethyl-amine selectivity (wt %) | Trimethyl-amine selectivity (wt %) | Methanol conversion rate (wt %) | Monomethyl-amine selectivity (wt %) | Dimethyl-amine selectivity (wt %) | Trimethyl-amine selectivity (wt %) |
| Example 1 | 92 | 35 | 60 | 5 | 90 | 38 | 59 | 3 |
| Example 2 | 96 | 35 | 58 | 7 | 93 | 36 | 59 | 5 |
| Example 3 | 92 | 37 | 60 | 3 | 89 | 40 | 58 | 2 |
| Example 4 | 90 | 37 | 61 | 2 | 85 | 41 | 58 | 1 |
| Example 5 | 95 | 35 | 59 | 6 | 91 | 35 | 60 | 5 |
| Example 6 | 95 | 35 | 58 | 7 | 91 | 36 | 58 | 6 |
| Example 7 | 92 | 37 | 60 | 3 | 89 | 39 | 59 | 2 |
| Example 8 | 93 | 36 | 59 | 5 | 91 | 37 | 59 | 4 |
| Example 9 | 96 | 36 | 60 | 4 | 92 | 37 | 60 | 3 |
| Comparative Example 1 | 92 | 37 | 57 | 6 | 82 | 37 | 53 | 10 |
| Comparative Example 2 | 92 | 36 | 58 | 6 | 85 | 39 | 53 | 8 |
| Comparative Example 3 | 89 | 37 | 60 | 3 | 85 | 40 | 58 | 2 |
| Comparative Example 4 | 95 | 33 | 59 | 8 | 87 | 38 | 54 | 8 |
| Comparative Example 5 | 70 | 41 | 49 | 10 | 65 | 44 | 48 | 8 |

Reaction conditions: temperature: 305° C., pressure: 2 MPa, and GHSV: 2500 h$^{-1}$

TABLE 3

| Section | 24 hours later | | | | 240 hours later | | | |
|---|---|---|---|---|---|---|---|---|
| | Methanol conversion rate (wt %) | Monomethyl-amine selectivity (wt %) | Dimethyl-amine selectivity (wt %) | Trimethyl-amine selectivity (wt %) | Methanol conversion rate (wt %) | Monomethyl-amine selectivity (wt %) | Dimethyl-amine selectivity (wt %) | Trimethyl-amine selectivity (wt %) |
| Example 10 | 98 | 35 | 62 | 3 | 95 | 38 | 60 | 2 |
| Comparative Example 6 | 96 | 33 | 60 | 7 | 92 | 37 | 58 | 5 |

Reaction conditions: temperature: 300° C., pressure: 2 MPa, and GHSV: 1500 h$^{-1}$

TABLE 4

| Section | 6 hours later | | | 240 hours later | | |
|---|---|---|---|---|---|---|
| | Monomethylamine conversion rate (wt %) | Dimethylamine selectivity (wt %) | Trimethylamine selectivity (wt %) | Monomethylamine conversion rate (wt %) | Dimethylamine selectivity (wt %) | Trimethylamine selectivity (wt %) |
| Example 11 | 76 | 99 | 1 | 72 | 98 | 2 |
| Comparative Example 7 | 74 | 99 | 1 | 68 | 95 | 5 |

Reaction conditions: temperature: 300° C., pressure: 2 MPa, and GHSV: 3000 h$^{-1}$

TABLE 5

| Section | 24 hours later | | | | 240 hours later | | | |
|---|---|---|---|---|---|---|---|---|
| | Methanol conversion rate (wt %) | Monomethyl-amine selectivity (wt %) | Dimethyl-amine selectivity (wt %) | Trimethyl-amine selectivity (wt %) | Methanol conversion rate (wt %) | Monomethyl-amine selectivity (wt %) | Dimethyl-amine selectivity (wt %) | Trimethyl-amine selectivity (wt %) |
| Example 12 | 93 | 31 | 62 | 7 | 87 | 38 | 60 | 2 |
| Comparative Example 8 | 89 | 31 | 59 | 10 | 75 | 39 | 56 | 5 |

Reaction conditions: temperature: 320° C., pressure: 2 MPa, and GHSV: 1200 h$^{-1}$ As is clear from Tables 2-5 above, the method for producing a methylamine compound according to the present invention maintains high dimethylamine selectivity and low trimethylamine selectivity and further realizes little reduction in the activity due to long-term use, and therefore has much industrial value.

The invention claimed is:

1. A method for producing a catalyst for use in the production of a methylamine compound, the catalyst comprising a modified crystalline silicoaluminophosphate salt molecular sieve, wherein the method comprises:
   a moisture control step of adsorbing moisture onto a crystalline silicoaluminophosphate salt molecular sieve in an amount of 5 to 30 wt % of the crystalline silicoaluminophosphate salt molecular sieve; and
   a step of heating the crystalline silicoaluminophosphate salt molecular sieve having moisture adsorbed thereon under a pressure of 0.1 MPa or more and at a temperature of 130 to 350° C. for 5 to 40 hours.

2. The method for producing a catalyst for use in the production of a methylamine compound according to claim 1, wherein the crystalline silicoaluminophosphate salt molecular sieve is at least one selected from SAPO-14, 17, 18, 21, 22, 25, 33, 34, 35, 39, 42, 43, 44, 47, 52 and 56.

3. The method for producing a catalyst for use in the production of a methylamine compound according to claim 1, wherein the crystalline silicoaluminophosphate salt molecular sieve comprises at least one element selected from among Mg, Ca, Sr, Y, Ti, Zr, V, Nb, Cr, Mn, Fe, Ru, Co, Rh, Ir, Ni, Pd, Pt, Cu, Zn, B, Ga, In, Ge and Sn.

4. The method for producing a catalyst for use in the production of a methylamine compound according to claim 1, wherein the moisture control step of adsorbing moisture onto the crystalline silicoaluminophosphate salt molecular sieve includes filling a reactor with the crystalline silicoaluminophosphate salt molecular sieve and continuously flowing a moisture-containing gas through a packed bed of the crystalline silicoaluminophosphate salt molecular sieve to be brought into contact therewith, and wherein the crystalline silicoaluminophosphate salt molecular sieve is brought into contact with the moisture-containing gas at a temperature higher than a dew point thereof.

5. The method for producing a catalyst for use in the production of a methylamine compound according to claim 4, wherein the moisture-containing gas is a mixed gas of water vapor and at least one selected from an inert gas and air.

6. A method for producing a methylamine compound which comprises performing a reaction between methanol and ammonia in the presence of a catalyst for use in the production of a methylamine compound comprising a crystalline silicoaluminophosphate salt molecular sieve, wherein the catalyst is produced by the method for producing a catalyst for use in the production of a methylamine compound according to claim 1.

7. A method for producing a methylamine compound which comprises performing a reaction between methanol and monomethylamine or a reaction between methanol, ammonia and monomethylamine in the presence of a catalyst for use in the production of a methylamine compound comprising a crystalline silicoaluminophosphate salt molecular sieve, wherein the catalyst is produced by the method for producing a catalyst for use in the production of a methylamine compound according to claim 1.

8. A method for producing a methylamine compound which comprises performing a disproportionation reaction of monomethylamine in the presence of a catalyst for use in the production of a methylamine compound comprising a crystalline silicoaluminophosphate salt molecular sieve, wherein the catalyst is produced by the method for producing a catalyst for use in the production of a methylamine compound according to claim 1.

\* \* \* \* \*